United States Patent [19]

King et al.

[11] Patent Number: 4,719,217

[45] Date of Patent: Jan. 12, 1988

[54] CERTAIN N-AZABICYCLOALKYL-BENZAMIDES USEFUL IN THE TREATMENT OF IMPAIRED GASTRO-INTESTINAL MOTILITY OR EMESIS

[75] Inventors: Francis D. King, Bishop's Stortford; Michael S. Hadley, Sawbridgeworth, both of England

[73] Assignee: Beecham Group p.l.c., Brentford, England

[21] Appl. No.: 878,993

[22] Filed: Jun. 26, 1986

[30] Foreign Application Priority Data

Jun. 28, 1985 [GB] United Kingdom ................. 8516371

[51] Int. Cl.$^4$ ................... A61K 31/445; C07D 471/08
[52] U.S. Cl. ..................................... 514/299; 546/112
[58] Field of Search ........................ 546/112; 514/299

[56] References Cited

U.S. PATENT DOCUMENTS 4,273,778  6/1981  Hadley et al. .................... 424/265

FOREIGN PATENT DOCUMENTS 0076592  4/1983  European Pat. Off. .
0013138  7/1983  European Pat. Off. .
3144183  8/1982  Fed. Rep. of Germany .
2145416  3/1985  United Kingdom .

*Primary Examiner*—Henry R. Jiles
*Assistant Examiner*—Bernhard I. Dentz
*Attorney, Agent, or Firm*—James F. Haley

[57] ABSTRACT

Compounds of formula (I) or a pharmaceutically acceptable salt thereof:

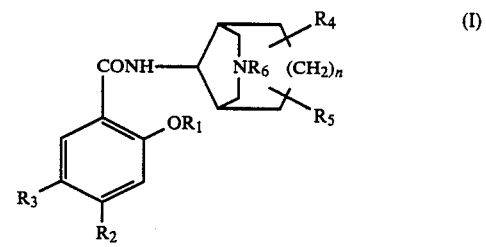

wherein:
$R_1$ is $C_{1-6}$ alkyl;
$R_2$ is amino or $C_{1-7}$ acylamino;
$R_3$ is halo or $C_{1-6}$ alkythio;
$R_4$ and $R_5$ are independently selected from hydrogen, $C_{1-6}$ alkyl, phenyl or phenyl $C_{1-4}$ alkyl any of which phenyl moieties may be substituted by one or two of halo, $CF_3$, $C_{1-6}$ alkoxy or $C_{1-6}$ alkyl;
$R_6$ is $C_{1-7}$ alkyl, —$(CH_2)_sR_7$, s being 0 to 2 and
$R_7$ being $C_{3-8}$ cycloalky, —$(CH_2)_tR_8$, t being 1 or 2 and
$R_8$ being thienyl or phenyl optionally substituted by one or two substituents selected from $C_{1-4}$ alkoxy, trifluoromethyl, halogen, nitro, carboxy, esterified carboxy and $C_{1-4}$ alkyl optionally substituted by hydroxy, $C_{1-4}$ alkoxy, carboxy, esterified carboxy or in vivo hydrolysable acyloxy; and
n is 0 to 3; having gastric motility enhancing activity and anti-emetic activity, a process for their preparation and their use as pharmaceuticals.

8 Claims, No Drawings

CERTAIN N-AZABICYCLOALKYL-BENZAMIDES USEFUL IN THE TREATMENT OF IMPAIRED GASTRO-INTESTINAL MOTILITY OR EMESIS

This invention relates to substituted benzamides having pharmacological activity, to a process for their preparation and to their use as pharmaceuticals.

U.K. patent application No. 2145416 discloses benzamides and benzoates having an alkylene bridged piperidyl side chain, and having serotonin M-antagonist activity.

A group of compounds have now been discovered which have gastro-intestinal motility enhancing activity and also anti-emetic activity.

Accordingly, the present invention provides a compound of formula (I) or a pharmaceutically acceptable salt thereof:

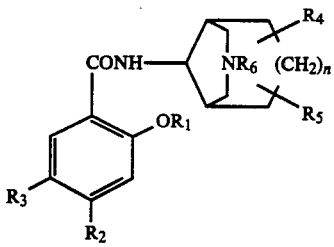

wherein:
$R_1$ is $C_{1-6}$ alkyl;
$R_2$ is amino or $C_{1-7}$ acylamino;
$R_3$ is halo or $C_{1-6}$ alkylthio;
$R_4$ and $R_5$ are independently selected from hydrogen, $C_{1-6}$ alkyl, phenyl or phenyl $C_{1-4}$ alkyl any of which phenyl moieties may be substituted by one or two of halo, $CF_3$, $C_{1-6}$ alkoxy or $C_{1-6}$ alkyl;
$R_6$ is $C_{1-7}$ alkyl, $-(CH_2)_s R_7$, s being 0 to 2 and $R_7$ being $C_{3-8}$ cycloalkyl, $-(CH_2)_t R_8$, t being 1 or 2 and $R_8$ being thienyl or phenyl optionally substituted by one or two substituents selected from $C_{1-4}$ alkoxy, trifluoromethyl, halogen, nitro, carboxy, esterified carboxy and $C_{1-4}$ alkyl optionally substituted by hydroxy, $C_{1-4}$ alkoxy, carboxy, esterified carboxy or in vivo hydrolysable acyloxy; and
n is 0 to 3.

Examples of $R_1$ include methyl, ethyl, n- and iso-propyl. Preferably $R_1$ is methyl.

Examples of $R_2$ include amino and $C_{1-6}$ alkanoylamino, such as formylamino, acetylamino, propionylamino, n- and iso-butyrylamino; and methyl. Often $R_2$ is amino or acetylamino, preferably amino.

Examples of $R_3$ include chloro, bromo, fluoro, methylthio, ethylthio, n- and iso-propylthio. Preferably $R_3$ is chloro or bromo, most preferably chloro.

Examples of $R_4$ and $R_5$ include hydrogen, methyl, ethyl, n- and iso-propyl, n-, iso-, sec- and tert-butyl, and phenyl, benzyl or phenethyl wherein any phenyl moiety is optionally substituted by one or two of fluoro, chloro, bromo, $CF_3$, methoxy, ethoxy, n- or iso-propoxy, methyl, ethyl, n- or iso-propyl.

Suitable examples of $R_6$, when $C_{1-7}$ alkyl, include methyl, ethyl, n- and iso-propyl and n-, iso-, sec- and tert-butyl. Within $C_{1-7}$ alkyl, $C_{5-7}$ alkyl are of interest and examples thereof include n-pentyl, n-hexyl, n-heptyl, 3-methylbutyl, 2,2-dimethylpropyl and 3,3-dimethylbutyl.

Suitable examples of $R_6$, when $-(CH_2)_s R_7$ are those wherein s is 1, in particular those wherein $R_7$ is $C_{5-8}$ cycloalkyl, such as cyclohexyl.

Suitable examples of $R_6$ when $-(CH_2)_t R_8$ are those wherein t is 1. $R_8$ may be 2- or 3-thienyl or preferably is phenyl optionally substituted by hydrogen, $C_{1-4}$ alkoxy, trifluoromethyl, halogen, carboxy, esterified carboxy or $C_{1-4}$ alkyl optionally substituted by hydroxy, $C_{1-4}$ alkoxy, carboxy, esterified carboxy and in vivo hydrolysable acyloxy.

When phenyl is substituted by optionally substituted $C_{1-4}$ alkyl, suitable examples of $C_{1-4}$ alkyl include methyl, ethyl, n- and iso-propyl, and n-, iso-, sec- and tert-butyl; methyl however, is preferred. Examples of substituents of such alkyl groups include hydroxy, methoxy, ethoxy, n- and iso- propoxy, carboxy, esterified carboxy, and in vivo hydrolysable acyloxy. The substitution preferably occurs on the terminal carbon atom of the alkyl group.

Examples of esterified carboxy groups include $C_{1-4}$ alkoxycarbonyl, such as methoxy-, ethoxy-, n- and iso-propoxy-carbonyl, phenoxycarbonyl or benzyloxycarbonyl, either being optionally substituted in the phenyl ring by one or two substituents selected from $C_{1-4}$ alkyl, $C_{1-4}$ alkoxy, trifluoromethyl, halogen or nitro.

Examples of in vivo hydrolysable acyloxy groups include $C_{2-6}$ alkanoyloxy, for example acetoxy, propionoxy, n- and iso- butyroxy, and 2,3 dimethylpropanyloxy, benzoyloxy or benzenesulphonyloxy either being optionally substituted in the phenyl ring by one or two substituents selected from $C_{1-4}$ alkyl, $C_{1-4}$ alkoxy, trifluoromethyl, halogen or nitro, or sulphonyloxy groups, for example $C_{1-6}$ alkanesulphonyloxy groups, such as methanesulphonyloxy.

$R_6$ is favourably $C_{1-7}$ alkyl, preferably methyl or ethyl.

n may be 0, 1, 2 or 3, preferably 0.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Examples of quaternary derivatives of the compounds of formula (I) include the compounds quaternised by compounds such as $R_{20}$-T wherein $R_{20}$ is $C_{1-6}$ alkyl, phenyl-$C_{1-6}$ alkyl or $C_{5-7}$ cycloalkyl, and T is a radical corresponding to an anion of an acid. Suitable examples of $R_{20}$ include methyl, ethyl and n- and iso-propyl; and benzyl and phenethyl. Suitable examples of T include halide such as chloride, bromide and iodide.

Examples of pharmaceutically acceptable salts also include internal salts such as pharmaceutically acceptable N-oxides.

The compounds of the formula (I) and their pharmaceutically acceptable salts, (including quaternary derivatives and N-oxides) may also form pharmaceutically acceptable solvates, such as hydrates, and these are included wherever a compound of formula (I) or a salt is herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

The amide moiety may be in an axial or equatorial orientation to the piperidyl ring of the azabicyclic side chain. The axial ($\beta$ or endo) orientation is preferred.

A group of compounds within formula (I) is of formula (II):

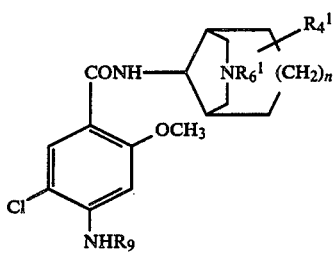

wherein
$R_9$ is hydrogen or acetyl;
$R_4^1$ is hydrogen or $C_{1-6}$ alkyl;
$R_6^1$ is $C_{1-7}$ alkyl;
and n is as defined in formula (I).

Examples and preferred values of the variable groups are as described for the corresponding groups under formula (I).

The invention also provides a process for the preparation of a compound of formula (I), or a pharmaceutically acceptable salt thereof which process comprises reacting a compound of formula (III):

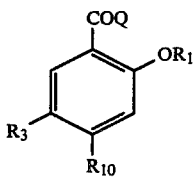

with a compound of formula (IV):

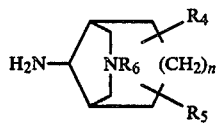

wherein Q is a leaving group; $R_{10}$ is $R_2$ or nitro; and the remaining variables are as hereinbefore defined, and thereafter optionally converting $R_{10}$ to $R_2$, $R_6$ to other $R_6$ and/or forming a pharmaceutically acceptable salt.

Examples of leaving groups Q, displaceable by a nucleophile include halogen such as chloro and bromo, hydroxy, carboxylic acyloxy such as $C_{1-4}$ alkanoyloxy or $C_{1-4}$ alkoxycarbonyloxy and activated hydrocarbyloxy such as pentachlorophenoxy.

If a group Q is a halide, then the reaction is preferably carried out at non-extreme temperatures in an inert non-hydroxylic solvent, such as benzene, dichloromethane, toluene, diethyl ether, tetrahydrofuran (THF) or dimethylformamide (DMF). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°-100° C., in particular 10°-80° C. are suitable.

If a group Q is hydroxy, then the reaction is generally carried out in an inert non-hydroxylic solvent, such as dichloromethane, THF or DMF optionally in the presence of a dehydrating catalyst, such as a carbodiimide, for example dicyclohexylcarbodiimide. The reaction may be carried out at any non-extreme temperature, such as −10° to 100° C., for example, 0° to 80° C. Generally, higher reaction temperatures are employed with less active compounds whereas lower temperatures are employed with the more active compounds.

If a group Q is carboxylic acyloxy, then the reaction is preferably carried in substantially the same manner as the reaction when Q is halide. Suitable examples of acyloxy leaving groups include $C_{1-4}$ alkanoyloxy and $C_{1-4}$ alkoxycarbonyloxy, in which case the reaction is preferably carried out in an inert solvent, such as methylene chloride, at a non-extreme temperature for example ambient temperatures in the presence of an acid acceptor, such as triethylamine. $C_{1-4}$ alkoxycarbonyloxy leaving groups may be generated in situ by treatment of the corresponding compound wherein Q is hydroxy with a $C_{1-4}$ alkyl chloroformate.

If a group Q is activated hydrocarbyloxy then the reaction is preferably carried out in an inert polar solvent, such as dimethylformamide. It is also preferred that the activated hydrocarbyloxy group is a pentachlorophenyl ester and that the reaction is carried out at ambient temperature.

Pharmaceutically acceptable salts of the compounds of this invention may be formed conventionally.

The salts may be formed for example by reaction of the base compound of formula (I) with a pharmaceutically acceptable organic or inorganic acid.

An $R_8$ group may be converted to an amino group by reduction; an $R_8$ $C_{1-7}$ acylamino substituent is convertible to an amino substituent by deacylation, and an amino substituent is convertible to a $C_{1-7}$ acylamino substituent by acylation with a carboxylic acid derivative. The reduction is carried out with a reagent suitable for reducing nitroanisole to aminoanisole; deacylation is carried out by treatment with a base such as an alkali metal hydroxide; acylation is carried out using, for example the corresponding acid chloride or free acid if formylation is to be carried out.

It will be appreciated that, $R_6$ when optionally substituted benzyl as hereinbefore defined, may be replaced by another group $R_6$.

Such $R_6$ benzyl groups may be removed for example when $R_2$ or $R_3$ is not halogen by conventional transition metal catalysed hydrogenolysis to give compounds of the formula (V):

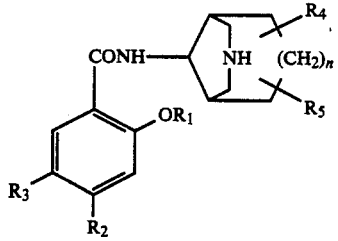

wherein the variable groups are as defined in formula (I).

This invention also provides an optional process step in the preparation of a compound of the formula (I) which comprises the reaction of a corresponding compound of the formula (V) as hereinbefore defined with a compound $Q_2R_6$ wherein $R_6$ is as defined in formula (I) and $Q_2$ is a leaving group, and optionally forming a pharmaceutically acceptable salt of the resulting compound of the formula (I).

Suitable values for $Q_2$ include groups readily displaced by nucleophiles such as Cl, Br, I, $OSO_2CH_3$ or $OSO_2C_6H_4pCH_3$.

Favoured values for $Q_2$ include Cl, Br and I.

Particularly suitably the compound $Q_2R_6$ is a benzyl halide, such as the bromide or chloride.

The reaction may be carried out under conventional alkylation conditions for example in an inert solvent such as dimethylformamide in the presence of an acid acceptor such as potassium carbonate. Generally the reaction is carried out at non-extreme temperature such as at ambient or at a slightly elevated temperature.

Converting $R_6$ to another $R_6$ in the compound of the formula (IV) before coupling with the compound of the formula (III), or its derivative is preferred. Such interconversions are effected conveniently under the above conditions. It is desirable to protect the amine function with a group readily removable by acidolysis such as a $C_{2-7}$ alkanoyl group before $R_6$ interconversion.

The substituents in the phenyl ring when $R_6$ is benzyl in a compound of formula (I), in particular the substituted $C_{1-4}$ alkyl substituents, are interconvertible. A number of such interconversions are possible not only for the end compounds of formula (I), but also for their intermediates as follows:

(i) a carboxy $C_{1-4}$ alkyl substituent is convertible to an esterified carboxy $C_{1-4}$ alkyl substituent by esterification;

(ii) an esterified carboxy $C_{1-4}$ alkyl substituent is convertible to a carboxy $C_{1-4}$ alkyl substituent by deesterification;

(iii) $C_{1-4}$ alkoxy $C_{1-4}$ alkyl substituent or an in vivo hydrolysable $C_{2-4}$ acyloxy $C_{1-4}$ alkyl substituent is convertible to an hydroxy $C_{1-4}$ alkyl substituent by hydrolysis;

(iv) an optionally esterified carboxy or carboxy $C_{1-3}$ alkyl substituent is convertible to an hydroxymethyl or hydroxy $C_{2-4}$ alkyl substituent by reduction; and (v) a hydroxy $C_{1-4}$ alkyl is convertible to $C_{1-4}$ alkyl by O-alkylation or to in vivo hydrolysable $C_{2-4}$ acyloxy $C_{1-4}$ alkyl by O-acylation.

Conversions (i) to (iv) are only examplary and are not exhaustive of the possibilities.

In regard to (i) and (ii), the esterification and edesterification reactions are carried out in conventional manner.

In regard to (iii), a $C_{1-4}$ alkoxy $C_{1-4}$ alkyl substituent is convertible to an hydroxy $C_{1-4}$ alkyl substituent by conventional methods, such as warming with aqueous hydrobromic acid or by treatment with pyridine hydrochloride, boron tribromide, boron triodide or iodotrimethylsilane.

An in vivo hydrolysable $C_{2-4}$ acyloxy $C_{1-4}$ alkyl substituent is convertible to an hydroxy $C_{1-4}$ alkyl substituent by acid or base hydrolysis.

In regard to (iv) the reduction is carried out with a selective metal complex hydride, for example lithium aluminium hydride, under conventional conditions.

In regard to (v), O-alkylation is carried out under conventional conditions in an inert solvent at a non-extreme temperature such as ambient temperature or slightly above or at reflux temperature. The $C_{1-4}$ alkylating agent has a leaving group that is readily displaceable by a nucleophile. Examples of leaving groups include halide, such as chloride, bromide or iodide, or labile acyloxy groups, such as mesyloxy and tosyloxy.

O-acylation is carried out under conventional conditions with an acylating agent which has an acyl group capable of forming an in vivo hydrolysable acyloxy group and a leaving group, such as halide, for example chloride and bromide, and hydrogen. When halide is the leaving group, the reaction is generally carried out in the presence of a base. When hydroxy is the leaving group, the reaction is generally carried out in the presence of a dehydrating agent, such as dicyclohexylcarbodiimide, in an inert solvent at non-extreme temperature, such as ambient temperature or slightly above, or reflux temperature.

Before carrying out any of these conversions, the effect, if any, on other substituents should be considered, and such reagents as are appropriate should be selected together with the adoption of such precautionary measures as are necessary. For example, O-alkylation and O-acylation may also produce N-alkylated and N-acylated products respectively unless the nitrogen atoms) is (are) previously protected.

This may be conveniently achieved by carrying out the alkylation or acylation reaction in a strong acid, such as trifluoroacetic acid, which protonates, and thereby protects, the nitrogen atom(s).

Compounds of the formula (V) are novel intermediates and thus form an aspect of the present invention.

Compounds of the formulae (III) and (IV) are known or are preparable analogously to, or routinely from, known compounds. Compounds of formula (IV) may be prepared from the corresponding ketones in the manner described in EP 13138 (or as described in U.K. patent application No. 2145416) and as described in the Description hereafter. The corresponding ketones are known or are prepared analogously.

It will be realised that in the resulting compound of the formula (I) the —CONH— linkage may have an α(or exo) or β (or endo) orientation with respect to the ring of the bicyclic moiety to which it is attached. A mixture of α and β isomers of the compound of the formula (I) may be synthesised non-stereospecifically and the desired isomer separated conventionally therefrom, for example by chromatography; or alternatively the α and β isomer may if desired be synthesised from the corresponding α or β form of the compound of the formula (IV).

The α or β form of the compound of the formula may if desired be prepared by known stereospecific processes, such as those leading to the α or β isomers of the compound of the formula (IV) described in EP 13138.

Compounds of the present invention have gastrointestinal motility enhancing activity and therefore may be used in disorders such as retarded gastric emptying, dyspepsia, flatulence, oesophagal reflux and peptic ulcer. The compounds of the present invention also have anti-emetic activity.

The invention also provides a pharmaceutical composition comprising a compound of formula (I), or a pharmaceutically acceptable salt thereof, or a pharmaceutically acceptable solvate of either of the foregoing and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of disorders relating to impaired gastrointestinal motility and/or emesis in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70kg adult will normally contain 0.5 to 1000 mg for example 1 to 500 mg, of the compound of the invention. Unit doses may be administered once or more than once a day, for example, 2, 3 or 4 times a day, more usually, 1 to 3 times a day, that is in the range of approximately 0.001 to 50 mg/kg/day, more usually 0.002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of disorders relating to impaired gastrointestinal motility and/or emesis.

The following Examples illustrate the preparation of compounds of formula (I); the following descriptions relate to intermediates thereto.

DESCRIPTION 1

(±) (8α,β)-3-Methyl-3-azabicyclo[3,2,1]octan-8-amine
(D1)

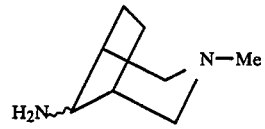

(D1)

3-Methyl-3-azabicyclo[3,2,1]octan-8-one (12.0 g) and hydroxylamine hydrochloride (12.0 g) in EtOH (300 ml) were heated under reflux for 4h. On cooling, the solid oxime hydrochloride was collected, dissolved in water (20 ml) and neutralised with solid $K_2CO_3$. Extraction with chloroform (3×100 ml) afforded the crude oxime (9.1 g). To a stirred suspension of $LiAlH_4$ (1.6 g) in dry THF (200 ml) at 0° C. was added conc. $H_2SO_4$ (1.2 ml). After 1h, a solution of 3.9 g of the crude oxime in THF (50 ml) was added and the reaction mixture heated under reflux for 18h. On cooling, 40% sodium hydroxide (3 ml) and water (3 ml) were added and the solid precipitate removed by filtration. Concentration and distillation of the filtrate afforded (D1) (1.6 g) bp 50°-54°/5 mm.

DESCRIPTION 2

(±) (10α)-8-Methyl-8-azabicyclo[4,3.1]-decan-10-amine (D2)

(D2)

3-Methyl-3-azabicyclo[4,3,1]decan-10-one (19.0 g) was converted to the title compound D2 (9.8 g) by the procedure outlined in Description 1.
b.p. 77°-78° C. at 3 mmHg.
Prepared similarly were :

DESCRIPTION 3

(±)(8α,β)-3-Ethyl-3-azabicyclo[3,2,1]octan-8-amine (D3)

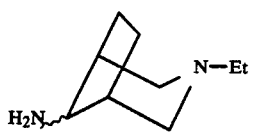
(D3)

b.p. 56°-62 °C. at 3 mmHg.

DESCRIPTION 4

(±)(8β)-3-Benzyl-3-azabicyclo[3,2,1]octan-8-amine (D4)

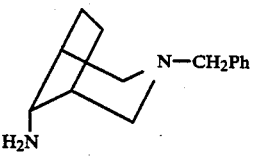
(D4)

b.p. 115°-25° C. at 0.1 mmHg

DESCRIPTION 5

(±)(9α,β)-3-Methyl-3-azabicyclo[3,3,1]nonan-9-amine (D5)

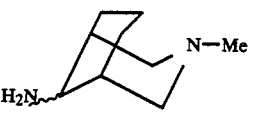
(D5)

A stirred solution of 3-methyl-3-azabicyclo[3,3,1]nonan-9-one oxime (3.1 g) in amyl alcohol (100 mls) was heated to gentle reflux and sodium (8.5 g) was added over 30 min. The reaction mixture was heated to reflux for a further 1.5 h, cooled to 80° C. and water (25 ml) added carefully. The aqueous layer was separated and the organic layer extracted with 5N HCl (2×25 ml). The acidic extracts were evaporated to dryness and basified with an excess (15 ml) of 40% NaOH solution and then saturated with solid K₂CO₃. The product was extracted into ether (3×50 ml) and the extracts dried (K₂CO₃) and distilled to give the title compound (2.1 g). b.p. 60°-62° C. at 3 mmHg.

EXAMPLE 1

(±)
(8β)-4-Amino-5-chloro-2-methoxy-N-(3-methyl-3-azabicyclo[3,2,1]octan-8-yl)benzamide (E1)

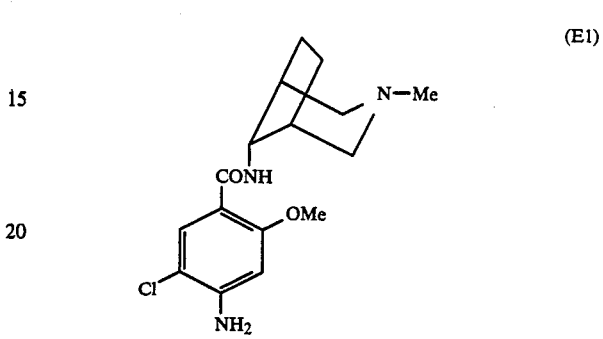
(E1)

A suspension of 4-acetamido-5-chloro-2methoxybenzoic acid (3.1 g) in dry CH₂Cl₂ (200 ml) was treated with oxalyl chloride (1.1 ml) and DMF (5 drops). After 1h, the clear solution was treated with a solution of the amine D1 (1.6 g) and triethylamine (3 ml) in CH₂Cl₂ (50 ml). After stirring at room temperature for 1h, the reaction mixture was washed with 10% Na₂CO₃ solution (50 ml), dried (K₂CO₃) and evaporated to dryness. Purification by column chromatography (silica, CHCl₃+2% MeOH) gave the acetamido derivative of E1 (2.9 g) mp 215°-8°. A solution of the acetamido derivative (2.9 g) in EtOH (100 ml) was heated under reflux with 10% sodium hydroxide solution (10 ml) for 1h. On cooling, the solvent was removed by rotary evaporation and the residue extracted with CHCl₃ (200 ml) and dried (K₂CO₃). Evaporation of the CHCl₃ and recrystallisation from EtOAc/CHCl₃/petrol afforded E1 (2.4 g) mp 224°-6°.

¹H-NMR (270 MHz, CDCl₃) 8.19 (1H, d), 8.01 (1H, s), 6.35 (1H, s), 4.50 (2H, brs), 4.13 (1H, dt), 3.95 (3H, s), 2.63 (2H, dd), 2.30 (2H, d), 2.29 (3H, s), 2.19 (2H, brs), 1.80 (4H, brs)

EXAMPLE 2

(±)
(8α)-4-Amino-5-chloro-2-methoxy-N-(3-methyl-3azabicyclo[3,2,1]octan-8-yl)benzamide (E2)

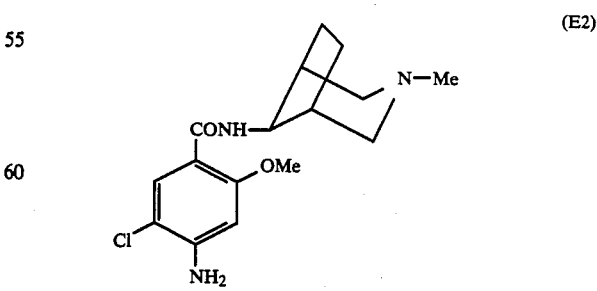
(E2)

Further elution with CHCl₃+5% MeOH of the column detailed in the procedure for E1 gave the more polar isomer as the acetamido derivative of E2 (2.0 g).

Hydrolysis in EtOH (100 ml) with 10% sodium hydroxide (8 ml) as described for E1 gave E2 (0.6 g) (from EtOAc/petrol) mp 192°–3° C.

¹H NMR (270 MHz, CDCl₃) 8.07 (1H, s), 7.67 (1H, d), 6.30 (1H, s), 4.47 (2H, brs), 3.97 (1H, d), 3.87 (3H, s), 2.78 (2H, dd), 2.29 (5H, d+s), 2.22 (2H, brs), 1.92–1.69 (4H, m)

Following the procedure outlined in Example 1, the following examples were prepared.

EXAMPLE 3

(±)(10α)-4-Amino-5-chloro-2-methoxy-N-(8-methyl-8-azabicyclo[4,3,1]decan-10-yl)benzamide (E3)

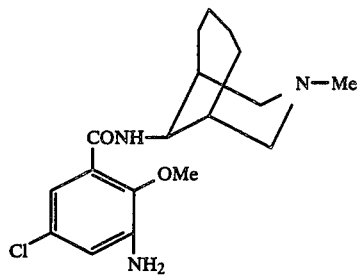

(E3)

mp 225°–6° C.

NMR (270 MHz, CDCl₃) δ8.12 (s, 1H), 8.11 (d, 1H), 6.31 (s, 1H), 4.41 (brs, 2H), 4.30 (dt, 1H), 3.90 (s, 3H), 2.64 (d, 2H),
2.28–1.98 (m, 9H),
1.90–1.45 (m, 6H)

EXAMPLE 4

(±)(8α)-4Amino-5-chloro-2-methoxy-N-(3-ethyl-3-azabicyclo[3,2,1]octan-8-yl)benzamide (E4)

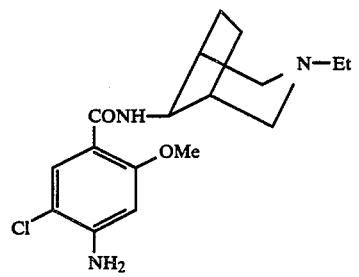

(E4)

mp 175°–6° C.

NMR (270 MHz, CDCl₃) δ8.09 (s, 1H), 7.70 (d, 1H), 6.29 (s, 1H), 4.40 (brs, 2H), 3 98 (brd, 1H), 3.89 (s, 3H), 2.92–2.75 (m, 2H), 2.40–2.32 (m, 2H), 2.30–2.15 (m, 4H), 1.90–1.60 (m, 4H), 1.03 (t, 3H)

EXAMPLE 5

(±)(8β)-4-Amino-5-chloro-2-methoxy-N-(3-ethyl-3-azabicyclo[3,2,1]octan-8-yl)benzamide (E5)

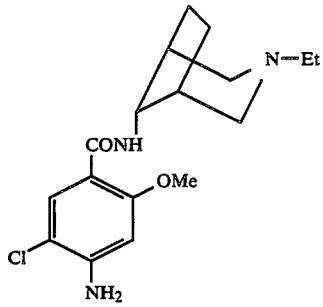

(E5)

mp 173°–4° C.

NMR (270 MHz, CDCl₃) δ8.19 (brd, 1H), 8.13 (s, 1H), 6.32 (s, 1H), 4.42 (brs, 2H), 4.15 (dt, 1H), 3.95 (s, 3H), 2.66 (brd, 2H), 2.42 (q, 2H), 2 27 (d, 2H), 2 19 (brs, 2H), 1.80 (brs, 4H), 1.06 (t, 3H)

EXAMPLE 6

(±)(8β)-4-Amino-5-chloro-2-methoxy-N-(3-benzyl-3-azabicyclo[3,2,1]octan-8-yl)benzamide (E6)

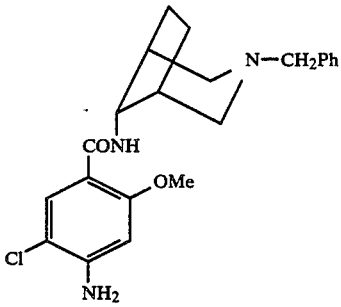

(E6)

mp 151°–3° C.

NMR (270 MHz, CDCl₃) δ8.20 (brd, 1H), 8.13 (s, 1H), 7.4–7.2 (m, 5H), 6.33 (s, 1H), 4.40 (brs, 2H), 4.14 (dt, 1H), 3.93 (s, 3H), 3.52 (s, 2H), 2.59 (dd, 2H), 2.35 (d, 2H), 2.17 (brs, 2H), 1.90–1.60 (m, 4H)

EXAMPLE 7

(±)(9β)-4-Amino-5-chloro-2-methoxy-N-(3-methyl-3-azabicyclo[3,3,1]nonan-9-yl)benzamide (E7)

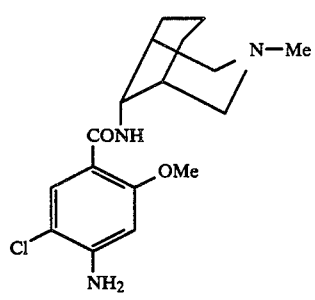

(E7)

A stirred suspension of 4-acetamido-5-chloro-2-methoxybenzoic acid (3.7 g) in dry CH₂Cl₂ (100 ml) was treated with oxalyl chloride (1.22 ml) and DMF (5 drops). After 1 h, the solvent was removed in vacuo and replaced with dry $CH_2Cl_2$ (100 ml). A solution of (±)(9α,β)-3-methyl-3-azabicyclo[3,3,1]nonan-9-amine (2.1 g) in $CH_2Cl_2$ (50 ml) was added and the mixture stirred at room temperature for 2 h. The precipitate was collected and dried. De-acetylation as described in Example 1 gave the title compound E7 (0.91 g).

mp 208°–11° C.

NMR (270 MHz, $CDC_3$) δ8.17 (brd, 1H), 8.11 (s, 1H), 6.32 (s, 1H), 4.38 (brs, 2H), 4.05 (dt, 1H), 3.95 (s, 3H), 2.74 (d, 2H), 2.46 (qt, 1H), 2.31 (brd, 2H), 2.16 (s, 3H), 1.95–1.70 (m, 6H), 1.52–1.40 (m, 1H)

EXAMPLE 8

(±)(9α)-4-Amino-5-chloro-2-methoxy-N-(3-methyl-3-azabicyclo[3,3,1]nonan-9-yl)benzamide (E8)

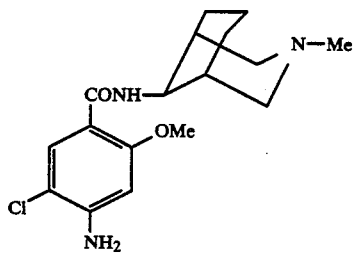

The filtrate obtained from the procedure for E7 was washed with aqueous $K_2CO_3$ solution and dried ($Na_2SO_4$). Evaporation to dryness gave a foam which was de-acetylated as described in Example 1 to give the title compound (1.62 g).

mp 214°–7° C.

NMR (270 MHz, $CDCl_3$) δ8.19 (brd, 1H), 8.08 (s, 1H), 6.32 (s, 1H), 4.41 (brs, 2H), 4.12–4.00 (m, 1H), 3.92 (s, 3H), 2.92 (brd, 2H), 2.65–2.30 (m, 3H), 2.16 (brs, 3H), 2.00–1.60 (m, 6H), 1.55–1.40 (m, 1H)

Pharmacological Data

1. Intragastric pressure in the rat

Intragastric pressure changes were recorded from fasted conscious and restrained rats using a saline filled catheter inserted into the lumen of the stomach via a permanent gastric fistula. The catheter was connected to a physiological pressure transducer and pressure changes recorded on a hot wire pen recorder. An index of activity was obtained by measuring the average height of pressure waves during 10 minute periods. Values for 4 such periods were obtained during assessment of spontaneous activity prior to dosing and for the 40 minute period following dosing with compound or vehicle. The Student's "t" test was applied to the mean values obtained for activity prior to and post treatment. Groups of 10 animals were used for each treatment.

The compound of Example 2 had an $ED_{50}$ of 0.5 mg/kg s.c.

2. Intraluminal pressure in the Heidenhain pouch of the dog

Pressure changes were recorded via a saline filled catheter inserted, with airtight closure, into the fistula of a chronic Heidenhain pouch of the previously fasted and lightly restrained conscious dog. The catheter was connected to a physiological pressure transducer and pressure changes recorded on a hot wire pen recorder.

Compounds were administered when the motility was in a phase of relatively low activity and the dose range determined which induced an increase in the amplitude of rhythmical contractions for a period of at least 4–5 minutes.

The results were as follows:

| Compound | $ED_{50}$ (mg/kg i.v.) |
|---|---|
| E1 | 0.05 |
| E2 | 0.05 |
| E5 | 0.01 |

We claim:

1. A compound of formula (I) or a pharmaceutically acceptable salt thereof:

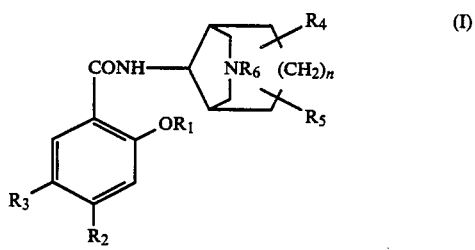

wherein:
$R_1$ is $C_{1-6}$ alkyl;
$R_2$ is amino or $C_{1-7}$ acylamino;
$R_3$ is halo or $C_{1-6}$ alkylthio;
$R_4$ and $R_5$ are independently selected from hydrogen, $C_{1-6}$ alkyl, phenyl or phenyl $C_{1-4}$ alkyl any of which phenyl moieties may be substituted by one or two of halo, $CF_3$, $C_{1-6}$ alkoxy or $C_{1-6}$ alkyl;
$R_6$ is $C_{1-7}$ alkyl, $-(CH_2)_sR_7$, s being 0 to 2 and $R_7$ being $C_{3-8}$ cycloalkyl, $-(CH_2)_tR_8$, t being 1 or 2 and $R_8$ being thienyl or phenyl optionally substituted by one or two substituents selected from $C_{1-4}$ alkoxy, trifluoromethyl, halogen, nitro, carboxy, esterified carboxy and $C_{1-4}$ alkyl optionally substituted by hydroxy, $C_{1-4}$ alkoxy, carboxy, esterified carboxy or in vivo hydrolysable acyloxy, wherein esterified carboxy is selected from the group consisting of $C_{1-4}$ alkoxy carbonyl, phenoxy carbonyl or benzyloxy carbonyl, either being optionally substituted in the phenyl ring by one or two substituents selected from $C_{1-4}$ alky, $C_{1-4}$ alkoxy, trifluoromethyl, halogen or nitro and in vivo hydrolysable acyloxy is selected from the group consisting of $C_{2-6}$ alkanoyloxy, benzoyloxy or benzene sulphonloxy, either being optionally substituted in the phenyl ring by one or two substituents selected from $C_{1-4}$ alkyl, $C_{1-4}$ alkoxy, trifluoromethyl, halogen or nitro, or sulphonyloxy groups; and n is 0 to 3.

2. A compound according to claim 1 wherein $R_1$ is methyl.

3. A compound according to claim 1 or 2 wherein $R_2$ is amino or acetylamino.

4. A compound according to claim 1, wherein $R_3$ is chloro or bromo.

5. A compound according to claim 1 of formula (II):

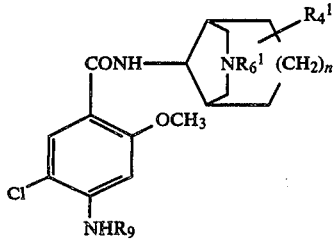

wherein $R_9$ is hydrogen or acetyl;

$R_4^1$ is hydrogen or $C_{1-6}$ alkyl;

$R_6^1$ is $C_{1-7}$ alkyl; and n is as defined in claim 1.

6. A compound selected from the group consisting of (±) (8β)-4-amino-5-chloro-2-methoxy-N-(3-methyl-3-azabicyclo[3,2,1]octan-8-yl)benzamide, (±) (8α)-4-amino-5-chloro-2-methoxy-N-(3-methyl-3-azabicyclo[3,2,1]octan-8-yl)benzamide, (±)(10α)-4-amino-5-chloro-2-methoxy-N-(8-methyl-8-aza-bicyclo[4,3,1]decan-10-yl)benzamide, (±)(8α)-4-amino-5-chloro-2-methoxy-N-(3-ethyl-3-aza-bicyclo[3,2,1]octan-8-yl)benzamide, (±)(8β)-4-amino-5-chloro-2-methoxy-N-(3-ethyl-3-aza-bicyclo[3,2,1]octan-8-yl)benzamide, (±)(8β)-4-amino-5-chloro-2-methoxy-N-(3-benzyl-3-aza-bicyclo[3,2,1]octan-8-yl)benzamide, (±)(9β)-4-amino-5-chloro-2-methoxy-N-(3-methyl-3-aza-bicyclo[3,3,1]nonan-9-yl)benzamide and (±) (9α)-4-amino-5-chloro-2-methoxy-N-(3-methyl-3-aza-bicyclo[3,3,1]nonan-9-yl)benzamide.

7. A pharmaceutical composition for the treatment of disorders relating to impared gastro-intestinal motility or emesis comprising an effective amount of compound according to any one of claims 1 to 6, or a pharmaceutically acceptable salt thereof, and a pharmaceutically acceptable carrier.

8. A method of treatment or prophylaxis of disorders relating to impaired gastro-intestinal motility or emesis in mammals, which comprises the administration of an effective amount of a compound according to claim 1 or a pharmaceutically acceptable salt thereof.

* * * * *